United States Patent [19]

Sunkel et al.

[11] Patent Number: 4,880,894
[45] Date of Patent: Nov. 14, 1989

[54] QUATERNARY AMMONIUM SALTS USED AS PHASE TRANSFER CATALYST

[75] Inventors: Carlos Sunkel; Miguel Fay de Casa Juana; Fernando Dorrego; Basilio Pando; Julio Alvarez-Builla; Juan J. Vaquero; Carlos Galera; María L. Vazquez, all of Madrid, Spain

[73] Assignee: Alter, S.A., Madrid, Spain

[21] Appl. No.: 251,032

[22] Filed: Sep. 26, 1988

Related U.S. Application Data

[63] Continuation of Ser. No. 116,398, Nov. 3, 1987, abandoned.

[30] Foreign Application Priority Data

Nov. 5, 1986 [GB] United Kingdom ................ 8626438

[51] Int. Cl.$^4$ ............................................. C07D 277/60
[52] U.S. Cl. ..................................... 548/152; 548/375; 548/445; 548/447; 548/469; 549/332; 558/10; 560/106; 562/408; 562/418; 564/92; 564/183; 564/256; 564/286; 564/292
[58] Field of Search .............. 564/286, 292, 256, 183, 564/92; 549/332; 548/152, 375, 469, 445, 447; 560/106; 562/408, 418; 558/10; 568/58, 630, 626, 814; 585/452

[56] References Cited

FOREIGN PATENT DOCUMENTS 567527 12/1958 Canada ................................. 564/292
744061 2/1956 United Kingdom ................ 564/292

Primary Examiner—Bruce Gray
Attorney, Agent, or Firm—Ladas & Parry

[57] ABSTRACT

Novel quaternary ammonium salts of general formula (I)

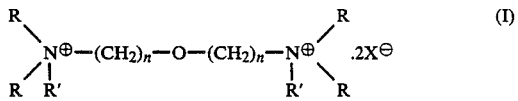

wherein:
R is a saturated or unsaturated, linear or branched alkyl radical of $C_1$ to $C_8$.
R' is a saturated or unsaturated, linear or branched alkyl radical of $C_1$ to $C_{12}$, or a benzyl radical.
n is a number equal to 2 or 3.
$X^\ominus$ is a halogenide anion, such as $Cl^\ominus$, $Br^\ominus$, $I^\ominus$, are used as phase transfer catalysts, in heterogeneous ionic reactions wherein the reagents are in different phase and have different polarity.

7 Claims, No Drawings

QUATERNARY AMMONIUM SALTS USED AS PHASE TRANSFER CATALYST

This is a continuation of co-pending application Ser. No. 116,398 filed on Nov. 3, 1987, now abandoned.

FIELD OF THE INVENTION

The present invention refers to the use of a series of quaternary ammonium salts as phase transfer catalysts, in heterogeneous ionic reactions wherein the reagents are in different phases and have different polarity.

These catalysts are specifically used, this not meaning a limitation, for improving the reaction among reagents in a medium wherein one of them is in a solid state or is an aqueous phase, being substantially immiscible with an adjacent organic phase, wherein the other reagent is. Consequently, a reaction in-between can only occur at the separation interphase or by transfer of a compound from one phase to another.

BACKGROUND

The quaternary ammoniym salts of the elements of Group V of the Periodic System, are characterized by being, generally, very stable strong alkalis, which are highly ionized in aqueous solution in order to form stable cations containing the pentavalent element bound to the hydrocarboned sustituents by covalent bonds.

It is known that these quaternary salts are, in some cases, more reactive than the corresponding K or Na salts.

On the other hand, if the configuration and the organic chains of the quaternary salt are adequate, these compounds are easily soluble in organic solvents.

The capability of these quaternary salts to catalyze transfer reactions has been widely studied (Starks, Ch. M. and Liotta, CH. "Phase Transfer Catalysis". Academic Press (1978)).

In general, the phase transfer catalysis is carried out in a two-phase system, an organic phase and the other an aqueous or solid phase.

The reagent being present, for instance, in the aqueous phase, is transferred to the organic one, by the transfer catalyst, according to the schedule:

Organic phase: Cat$^+$Y$^-$ +  $\longrightarrow$ Cat$^+$X$^-$ + 

Aqueous phase: Cat$^+$Y$^-$ + $\boxed{X^-}$ $\longleftarrow$ Cat$^+$X$^-$ + $\boxed{Y^-}$ The reactions which can be carried out by this method are numerous and, as an example, the following can be cited: C-alkylizations, O-alkylizations, esterifications, halogen exchange, ester and chloride hydrolysis, carbene reactions and, in general, nucleophilic displacements of the kind:

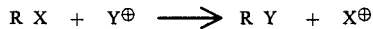

wherein Y can be for instance: Cl$^-$, Br$^-$, I$^-$, —COO$^-$, —NO$_2^-$, —NCO$^-$, —OH$^-$, —CN$^-$, —SCN$^-$.

A great number of these reactions are described by Keller, W. E. "Compendium of Phase-Transfer Reactions and Related Synthetic Methods", Fluka A. G. (1979).

The ammonium salt amount necessary to catalyze a reaction varies substantially depending on the type of reaction and the catalyst used. The reaction rate generally increases when the catalyst amount, the temperature or both, are increased.

In general, the catalyst amount used varies in the range between the 0.01% and the 50% by weight, with reference to the reagent in the least polar phase.

Besides ammonium salts, the following compounds may be used as phase transfer catalysts: phosphonium salts, crown ethers, microbicyclic compounds and polyethylene glycols.

Each one of them has specific disadvantages: quaternary salts usually have little stability, crown ethers and macrobicyclic compounds are expensive and toxic and polyethylene glycols are little effective.

DESCRIPTION OF THE INVENTION

The present invention refers to the use of a series of quaternary ammonium salts as phase transfer catalysts.

These quaternary ammonium salts have a general structure (I)

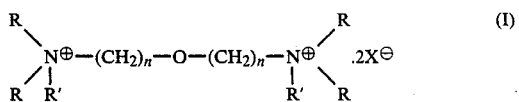

wherein:

R is a saturated or unsaturated, linear or branched, alkyl radical of $C_1$ to $C_8$. R' is a saturated or unsaturated, linear or branched, alkyl radical of $C_1$ to $C_{12}$, or a benzyl radical.

n is a number equal to 2 or 3.

X$^\theta$ is a halogenide: Cl$^\theta$, Br$^\theta$, I$^\theta$.

Some of the derivatives included in general formula (I) are shown below:

(a) Bis-[2-(N-benzyl-N,N-diethylammonium)ethyl]ether, dichloride (compound 1)

(b) Bis-[2-(N-benzyl)-(N,N-diethylammonium)ethyl]ether, dibromide (compound 2).

(c) Bis-[2-(N,N-diethyl-N-methylammonium)ethyl]ether, diiodide (compound 3).

(d) Bis-[3-(N-benzyl-N,N-dimethyl)1-propyl]ether, dichloride (compound 4).

(e) Bis-[2-(N-benzyl-N,N-dimethyl)ethyl]ether dichloride (compound 5).

(f) Bis-[2-N,N,N-triethyl)-ethyl]ether, dibromide (compound 6).

(g) Bis-[3-(N,N-dimethyl-N-ethyl)-1-propyl]ether, dibromide (compound 7).

(h) Bis-[2-[N,N-diethyl-N-(1-propyl)]ethyl]ether, dibromide (compound 8).

(i) Bis-[3-[N,N-dimethyl-N-(1-propyl)]1-propyl]ether, dibromide (compound 9).

(j) Bis-[2-[N,N-dimethyl-N-(1-propyl)]ethyl]ether, dibromide (compound 10).

(k) Bis-[2-[N,N-diethyl-N-(1-butyl)]ethyl]ether, dibromide (compound 11).

(l) Bis-[3-[N,N-dimethyl-N-(1-butyl)]1-propyl]ether, dibromide (compound 12).

(m) Bis-[2-[N,N-diethyl-N-(1-pentyl)]ethyl]ether, dibromide (compound 13).

(n) Bis-[3-[N,N-dimethyl-N-(1-pentyl)]propyl]ether, dibromide (compound 14).

(o) Bis-[2-[N,N-diethyl-N-(1-hexyl)]ethyl]ether, dibromide (compound 15).

(p) Bis-[3-[N,N-dimethyl-N-(1-hexyl)]propyl]ether, dibromide (compound 16).

(q) Bis-[2-[N,N-diethyl-N-(1-octyl)]ethyl]ether, dibromide (compound 17).

(r) Bis-[3-[N,N-dimethyl-N-(1-octyl)]propyl]ether, dibromide (compound 18).

(s) Bis-[2-[N,N-dimethyl-N-(1-octyl)]ethyl]ether, dibromide (compound 19).

(t) Bis-[2-(N,N-diisopropyl-N-methyl)ethyl]ether, diiodide (compound 20).

(u) Bis-[3-(N,N,N-trimethyl)propyl]ether, diiodide (compound 21).

In examples 1 to 26, hereinfter exposed, the use, in different reactions, of some of the catalysts obtained, is illustrated, comparing the effectiveness thereof with that of others already known:

C-ALKYLATION

Example 1

Phenylacetonitrile (5.85 g, 0.05 mol), 0.1 mol of 1-bromobutane, 50% aqueous sodium hydroxide (20 ml) and 0.0015 mol of compound 1 were stirred at room temperature for 24 hours. At the end of that time, the reaction mixture was diluted with methylene chloride (20 ml) and the organic phase was separated, washed with water (3×10 ml) and dried over magnesium sulphate. The solvent and the excess of alkylating agent were removed under reduced pressure and the residue was analyzed by GLC. Monoalkylated product: 70%. Dialkylated product: 22%.

The same conditions as above using tetra-n-butylammonium bromide as catalyst yielded 61% of monoalkylation product and 27% of dialkylation product.

O-ALKYLATION

Examples 2 to 5

A mixture of phenol (1.89 g, 20 mmol), alkylating agent (40 mmol), 5% aqueous sodium hydroxide solution (50 ml), 1 mmol of the catalyst and the suitable solvent (40 ml) was stirred under the conditions given in Table 1. The organic layer was then separated and the aqueous layer extracted twice with 20 ml portions of the solvent used in the reaction. The combined organic extracts were evaporated, the residue mixed with water and the mixture extracted with ether. The organic extract was washed twice with 2N ammonia solution (when dimethyl sulphate was used as alkylating agent), 2N sodium hydroxide solution, and finally with saturated sodium chloride solution. After drying with sodium sulphate, the solvent was evaporated and the residual ether purified by distillation.

TABLE 1

Preparation of phenol ethers.

| Catalyst | Alkylating Agent | Solvent | Temp. (°C.) | Time (h) | Yield (%) |
|---|---|---|---|---|---|
| Compound 1 | $(CH_3)_2SO_4$ | $CH_2Cl_2$ | r.t. | 10 | 40 |
| TBAB | $(CH_3)_2SO_4$ | $CH_2Cl_2$ | r.t. | 10 | 79 |
| Compound 1 | $BrCH_2CO_2Et$ | $CH_2Cl_2$ | r.t. | 10 | 40 |
| TBAB | $BrCH_2CO_2Et$ | $CH_2Cl_2$ | r.t. | 10 | 72 |
| Compound 1 | $(CH_3)_2SO_4$ | Benzene | 60–70 | 5 | 65 |
| Compound 4 | $(CH_3)_2SO_4$ | Benzene | 60–70 | 5 | 66 |

TBAB = Tetra-n-butylammonium bromide.

Examples 6 to 10

Benzoic acid (2.44 g, 0.02 mol), benzyl chloride (0.021–0.063 mol), finely powdered potassium carbonate (26.56 g, 0.19 mol), dichloromethane (30 ml) and 0.8 mmol of the catalyst were stirred under reflux for the time indicated in Table 2. The reaction was stopped by careful addition of water (30 ml) and the organic phase was separated. The aqueous layer was extracted with dichloromethane (2×15 ml) and the combined organic extracts were washed with sodium hydrogen carbonate, dried over magnesium sulphate and evaporated to give the benzyl benzoate, which are purified by distillation.

TABLE 2

Preparation of benzyl benzoate.

| Catalyst | RX (eq.) | Time (h) | Yield (%) |
|---|---|---|---|
| Compound 1 | 0.021 | 2 | 11 |
| Compound 1 | 0.021 | 6 | 45 |
| Compound 1 | 0.021 | 10 | 62 |
| Compound 1 | 0.063 | 2 | 71 |
| Compound 11 | 0.021 | 10 | 62 |

Example 11

A mixture of n-butanol (0.74 g, 0.01 mol), benzyl chloride (2.53 g, 0.02 mol), 50% aqueous sodium hydroxide solution (10 ml) and 0.5 mol of compound 1 was stirred at 50°–60° C. for 4 hours. The reaction mixture was allowed to cool to room temperature and diluted with dichloromethane (10 ml). The organic layer was separated and the aqueous layer extracted twice with 10 ml portions of dichloromethane. The combined organic extracts were evaporated, the residue mixed with water and the mixture extracted with ether. The organic extract was washed twice with 2N sodium hydroxide solution and saturated sodium chloride solution. After drying with magnesium sulphate, the solvent was evaporated and the residual benzyl-n-butyl ether purified by distillation.

Yield: 90%.

The same conditions as above, using tetra-n-butyl ammonium bromide as catalyst yielded 76% of the ether.

Example 12

A mixture of benzophenone oxime (1.97 g, 0.01 mol), benzyl chloride (1.58 g, 0.0125 mol), 50% sodium hydroxide solution (8 ml), benzene (5 ml) and compound 1 (0.5 mol) was stirred at 80° C. for 4 hours and then poured into hot water and left overnight at room temperature. The solid thus obtained was filtered off, washed with water and dried. Recrystallization from methanol gave pure benzophenone o-(benzyl)oxime. Yield: 90%. m.p.: 56°–58° C.

The reaction and work-up were also carried out as above described, using tetra-n-butylammonium bromide as catalyst.

Yield: 87%.

N-ALKYLATION

Examples 13 and 14

1-Bromobutane (1.51 g, 0.011 mol) in benzene (10 ml) was slowly added to a refluxing mixture of benzamide (1.21 g, 0.01 mol), 50% aqueous sodium hydroxide solution (10 ml) and 1 mmol of the catalyst (Table 3). After the addition of has been completed, refluxing is continued for 4 hours. The reaction mixture was then cooled to room temperature and diluted with water (20 ml). The organic phase is separated, washed with water (3×10 ml) until neutral, dried over magnesium sulphate and evaporated to give pure N-n-butylbenzamide. Yields are given in Table 3.

TABLE 3

Preparation of N—n-butylbenzamide.

| Catalyst | Yield (%) |
|---|---|
| Compound 1 | 30 |
| Compound 4 | 53 |
| TBA-HSO$_4$ | 77 |

TBA-HSO$_4$ = Tetra-n-butylammonium hydrogensulphate.

Examples 15 and 16 n-Butyl bromide or benzyl chloride (0.0125 mol) was added to a mixture of carbazole (1.67 g, 0.01 mol), 50% aqueous sodium hydroxide (10 ml), benzene (2 ml) and 0.3 mmol of the catalyst (Table 4). The reaction mixture was stirred at 70°-80° C. for 1 hour and then poured into hot water and left overnight ar room temperature. The solid thus obtained was filtered off, washed with water and dried. Recrystallization from ethanol afforded N-alkylated carbazoles.

TABLE 4

Preparation of N—Alkylcarbazoles.

| Catalyst | R-Y | Yield (%) | m.p. (°C.) |
|---|---|---|---|
| Compound 1 | n-C$_4$H$_9$Br | 82 | 58 |
| TEBAC | n-C$_4$H$_9$Br | 82 | 58 |
| Compound 1 | Ph-CH$_2$Cl | 80 | 117–118 |
| TEBAC | Ph-CH$_2$Cl | 75 | 117–118 |

TEBAC = Triethylbenzylammonium chloride.

Example 17

Benzyl chloride (2.78 g, 0.022 mol) in benzene (10 ml) was added with efficient stirring to a refluxing mixture of benzene sulfonamide (1.57 g, 0.01 mol), 50% aqueous sodium hydroxide (10 ml) and 1 mmol of compound 1. The reaction mixture was heated under reflux for 4 hours and then allowed to cool to room temperature. After dilution with water (20 ml), the organic phase was separated, washed with water (3×10 ml) until neutral, dried with magnesium sulphate and evaporated to give a solid residue which was recrystallized from ethanol to yield pure N,N-dibenzylsulfonamide. Yield: 82%. m.p.: 67°-68° C.

The reaction and work-up were carried out as above described using tetra-n-butylammonium bromide as catalyst.

Yield: 87%.

Example 18

Indole (1.17 g, 0.01 mol) was added to a mixture of benzyl chloride (1.90 g, 0.015 mol), 50% aqueous sodium hydroxide solution (5 ml), benzene (10 ml) and 0.5 mmol of compound 1. The mixture was stirred at 60°-70° C. for 5 hours, then cooled to room temperature and diluted with water (10 ml). The organic layer was separated, washed with diluted hydrochloric acid, water and dried over anhydrous magnesium sulphate. The solvent and excess of benzyl chloride were removed under vacuo and the residue was chromatographed on silica gel using n-hexane to give the N-benzylindole (70%), m.p.: 43°-45° C.

Following this procedure, N-benzylindole was obtained in 85% and 90% yield using triethylbenzylammonium chloride and tetra-n-butylammonium hydrogensulphate catalyst respectively.

Example 19

A mixture of 2-methylbenzimidazole (1.32 g, 0.01 mol), 1-bromobutane (1.21 g, 0.01 mol), 50% aqueous sodium hydroxide (5 ml), toluene (20 ml) and 0.5 mmol of compound 1 was stirred at 80°-85° C. for 3 hours. After that time, the resulting mixture was allowed to cool to room temperature and the organic layer was separated, extracted with concentrated hydrochloric acid (3×20 ml). The acidic solution was neutralized with 20% sodium hydroxide, extracted with toluene (3×15 ml), dried over magnesium sulphate and evaporated to give a residue which was distilled at reduced pressure (0.4–0.5 mm 162°-6° C.) to give 1-n-butyl-2-methylbenzimidazole. Yield: 65%.

The reaction carried out using tetra-n-butylammonium bromide as catalyst afforded the alkylated product in 91% yield.

S-ALKYLATION

Example 20

Sodium sulphide nonahydrate (2.40 g, 0.01 mol), benzyl chloride (1.26 g, 0.01 mol), water (3 ml) and compound 1 (0.5 mmol) were stirred at 70°-78° C. for 20 minutes. The reaction mixture was poured into water and left overnight at room temperature. The white crystals thus obtained were filtered off and dried to give 2.02 g of benzyl sulphide.

Yield: 94% m.p.: 47°-48° C.

Under the same conditions, the same yield was obtained using tetra-n-butylammonium bromide as catalyst.

Example 21

A mixture of potassium thiocyanate (29.1 g, 0.3 mol), 1-bromobutane (19.1 g, 0.14 mol), water (30 ml) and compound 1 (4 mmol) was stirred under reflux for 75 minutes. Then, the mixture was cooled to room temperature, the organic layer separated and the aqueous phase extracted with ether. After drying over magnesium sulphate the combined organic portions, the solvent was evaporated and the residue distilled at reduced pressure (30 mm) to give n-butyl thiocyanate (80% yield).

Following this procedure, the alkylated thiocyanate was obtained in 84% yield if tetra-n-butylammonium bromide is used as catalyst.

OXIDATION

Examples 22 and 23

Potassium permanganate (3.16 g, 0.02 mol) in water (35 ml) was stirred for 10 minutes and then cooled in a water bath while phenylacetonitrile or benzyl alcohol (0.011 mol), benzene (20 ml) and the catalyst (Table 5) (1mmol) were added. The mixture was stirred for 3 hours at room temperature and worked up by addition of 4% sodium bisulphite (60 ml), acidification with 2N hydrochloric acid, separation of organic layer and extraction of the aqueous layer with benzene (2×20 ml). The combined organic extracts were dried over magnesium sulphate and the solvent evaporated on a rotary evaporator. Recrystallization of the solid residue obtained gives pure benzoic acid.

TABLE 5

Preparation of Benzoic Acid.

| Catalyst | Starting Material | Yield (%) |
|---|---|---|
| Compound 1 | Phenylacetonitrile | 63 |
| TBAB | Phenylacetonitrile | 60 |
| Compound 1 | Benzyl alcohol | 75 |
| TBAB | Benzyl alcohol | 76 |

TBAB = Tetra-n-butylammonium bromide.

REDUCTION

Example 24

Acetophenone (6 g, 0.05 mol), benzene (15 ml), sodium borohydride (1.13 g, 0.03 mol), water (15 ml) and compound 1 (3 mmol) were vigorously stirred at room temperature for 6 hours. The organic layer was then separated, the aqueous phase extracted with dichloromethane (3×15 ml) and the combined organic fractions dried over magnesium sulphate. After evaporation of the solvent, the residue was chromatographed on silica gel. Racemic 1-phenylethanol was eluted with n-hexane.

Yield: 70%.

Under the same conditions, the reduction of acetophenone using tetra-n-butylammonium hydrogensulphate as catalyst gave racemic 1-phenylethanol in 90% yield.

ALDOL-TYPE REACTION

Example 25

A mixture of 2-methylbenzothiazole (1.49 g, 0.01 mol), benzaldehyde (1.27 g, 0.012 mol), 50% sodium hydroxide solution (3 ml), toluene (5 ml) and compound 1 (1 mmol) was stirred at reflux temperature for 4 hours. The reaction mixture was allowed to cool to room temperature and then diluted with water (10 ml). The organic layer was separated and the aqueous phase extracted with toluene. The combined organic portions were dried over magnesium sulphate and evaporated to give a solid residue which was crystallized from ethanol to give the corresponding 2-styrylbenzothiazole.

Yield: 57%. m.p. 109°–110° C.

The reaction carried out in the presence of tetra-n-butylammonium hydrogensulphate as catalyst gives styryl derivative in 72% yield.

REFORMATSKY-TYPE REACTION

Example 26

To a stirred mixture of cyclohexanone (5.39 g, 0.055 mol), 50% sodium hydroxide solution (10 ml) and compound 1 (1 mmol) was added dropwise chloroacetonitrile (3.8 g, 0.05 mol) and stirring was continued for further 45 minutes. After that time, the resulting reaction mixture was diluted with dichloromethane (15 ml), the organic layer was separated and the aqueous phase extracted with dichloromethane (3×15 ml). The combined organic portions were dried over magnesium sulphate and evaporated to give a residue which upon distillation under reduced pressure gave 1-oxaspiro[2,5]octane-2-carbonitrile.

Yield: 46%. b.p.: 85° C./5 mm Hg.

The glicidic nitrile was obtained in 52% yield by using triethylbenzylammonium chloride as catalyst.

We claim:

1. A method for catalyzing heterogenous ionic reactions where the reaction reagents are in different phases and have different polarity comprising introducing quaternary ammonium salts of formula (I)

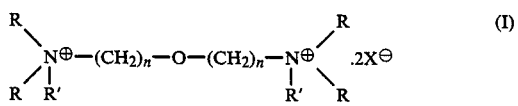

wherein;

R is a saturated or unsaturated, linear or branched alkyl radical of $C_1$ to $C_8$ R is a saturated or unsaturated, linear or branched alkyl radical of $C_1$ to $C_{12}$, or a benzyl radical n is a number equal to 2 or 3

$X^-$ is a halogenide anion, such as $Cl^-$, $Br^-$, $I^-$, into said reactions to catalyse said reactions.

2. The method, as in claim 1 wherein the compound of formula I is selected from the group consisting of (a) Bis-[2-(N-benzyl-N,N-diethylammonium)ethyl]ether, dichloride
(b) Bis-[2-(N-benzyl)-(N,N-diethylammonium)ethyl]ether, dibromide
(c) Bis-[2-(N,N-diethyl-N-methylammonium)ethyl]ether, diiodide
(d) Bis-[3-(N-benzyl-N,N-dimethyl)1-propyl]ether, dichloride
(e) Bis-[2-(N-benzyl-N,N-dimethyl)ethyl]ether dichloride
(f) Bis-[2-(N,N,N-triethyl)-ethyl]ether, dibromide
(g) Bis-[3-(N,N-dimethyl-N-ethyl)-1-propyl]ether, dibromide
(h) Bis-[2-[N,N-diethyl-N-(1-propyl)]ethyl]ether, dibromide
(i) Bis-[3-[N,N-dimethyl-N-(1-propyl)]1-propyl]ether, dibromide
(j) Bis-[2-[N,N-dimethyl-N-(1-propyl)]ethyl]ether, dibromide
(k) Bis-[2-[N,N-diethyl-N-(1-butyl)]ethyl]ether, dibromide
(l) Bis-[3-[N,N-dimethyl-N-(1-butyl)]1-propyl]ether, dibromide
(m) Bis-[2-[N,N-diethyl-N-(1-pentyl)]ethyl]ether, dibromide
(n) Bis-[3-[N,N-dimethyl-N-(1-pentyl)]propyl]ether, dibromide
(o) Bis-[2-[N,N-diethyl-N-(1-hexyl)]ethyl]ether, dibromide
(p) Bis-[3-[N,N-dimethyl-N-(1-hexyl)]propyl]ether, dibromide
(q) Bis-[2-[N,N-diethyl-N-(1-octyl)]ethyl]ether, dibromide
(r) Bis-[3-[N,N-dimethyl-N-(1-octyl)]propyl]ether, dibromide
(s) Bis-[2-[N,N-dimethyl-N-(1-octyl)]ethyl]ether, dibromide
(t) Bis-[2-(N,N-diisopropyl-N-methyl)ethyl]ether, diiode
(u) Bis-[3-(N,N,N-trimethyl)propyl]ether, diiodide.

3. The method, as in claim 1 wherein the heterogenous ionic reaction is one selected from the group consisting of C-alkylizations, O-alkylizations, esterifications, halogen exchanges, ester and chloride hydrolysis, carbene displacements and nucleophilic displacements wherein the reaction proceeds as follows:

$$RX + Y_- \rightarrow RY + X_-$$

wherein Y is $Cl_-$, $Br_-$, $I_-$, $-COO_-$, $-NO_2^-$, $NCO_-$, $OH_-$, $CN_-$, $-SCN_-$ 4. The method, as in claim 3 wherein the reaction takes place in a medium wherein one reagent is in a solid state or is in an aqueous phase, being substantially immiscible with an adjacent organic phase in which the other reagent is present.

5. The method, as in claim 4 wherein the amount of compound of Formula I used to catalyze the reaction is between 0.01% and 50% by weight with reference to the reagent in the least polar phase.

6. The method as in claim 5 wherein the reaction occurs at room temperature.

7. The method as in claim 6 wherein the reaction occurs at 70°–78° C.

* * * * *